United States Patent [19]

Hazen et al.

[11] 4,374,772
[45] Feb. 22, 1983

[54] PROCESS FOR THE PREPARATION OF N-FORMIMIDOYL THIENAMYCIN AND REAGENTS THEREFOR

[75] Inventors: George G. Hazen, Westfield; Ralph P. Volante, East Windsor; Kenneth E. Wilson, Westfield, all of N.J.

[73] Assignee: Merck & Co., Inc., Rahway, N.J.

[21] Appl. No.: 244,934

[22] Filed: Mar. 19, 1981

[51] Int. Cl.³ .......................................... C07D 487/04
[52] U.S. Cl. .............................................. 260/245.2 T
[58] Field of Search ................................... 260/245.2 T

[56] References Cited

U.S. PATENT DOCUMENTS 4,194,047  3/1980  Christensen et al. ......... 260/245.2 T

FOREIGN PATENT DOCUMENTS 6639  1/1980  European Pat. Off. ...... 260/245.2 T

Primary Examiner—Mary C. Lee
Attorney, Agent, or Firm—James A. Arno; Hesna J. Pfeiffer

[57] ABSTRACT

Disclosed is a novel class of substituted and unsubstituted benzyl formimidates, represented in a convenient acid addition salt form (I); and the use of these reagents in the preparation of the antibiotic N-formimidoyl thienamycin (II):

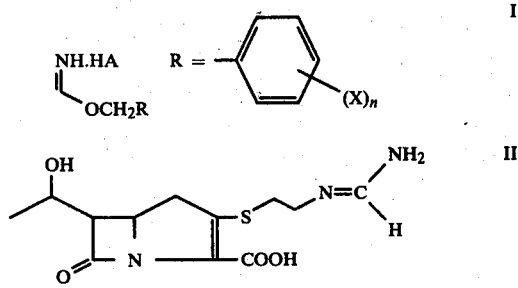

wherein A is a non-critical anion such as chloro, bromo, hydrogen sulfate or an alkyl aralkyl or aryl sulfonate, wherein the alkyl moiety has 1–6 carbon atoms and the aryl moiety is phenyl, for example; n is 0, 1 or 2; and X is independently selected from nitro, halo (chloro, bromo, fluoro, and iodo), loweralkyl having from one to six carbon atoms, phenyl, and phenylalkyl having from 7–12 carbon atoms, and —COOR, wherein R is hydrogen or loweralkyl having from one to six carbon atoms.

1 Claim, No Drawings

PROCESS FOR THE PREPARATION OF N-FORMIMIDOYL THIENAMYCIN AND REAGENTS THEREFOR

BACKGROUND OF THE INVENTION

This invention relates to a process for preparing N-formimidoyl thienamycin (II) from thienamycin (III) in reaction with certain substituted and unsubstituted benzyl formimidates (I):

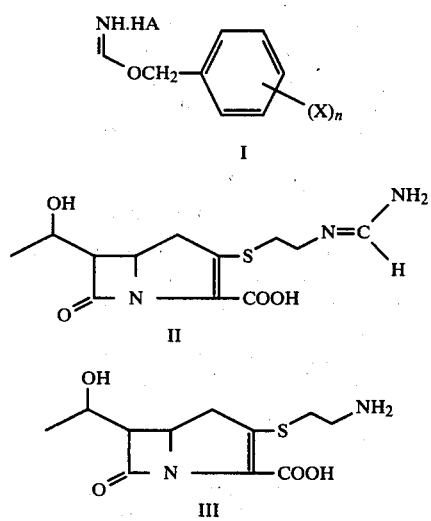

wherein A is a non-critical anion such as chloro, bromo, hydrogen sulfate, or an alkyl, aralkyl or aryl sulfonate, wherein the alkyl moiety has 1-6 carbon atoms and the aryl moiety is phenyl, for example; X is independently selected from the group consisting of nitro, halo (chloro, bromo, fluoro, and iodo), loweralkyl having from one to six carbon atoms, phenyl, and phenylalkyl having from 7-12 carbon atoms, and —COOR, wherein R is hydrogen or loweralkyl having from one to six carbon atoms; and n is an integer selected from 0, 1, or 2.

N-Formimidoyl thienamycin and thienamycin are both known antibiotics. See for example U.S. Pat. No. 4,194,047 (Mar. 18, 1980) which discloses N-formimidoyl thienamycin and a method for its synthesis from thienamycin. The present process for the preparation of N-formimidoyl thienamycin (II) proceeds via the reaction of reagent I with thienamycin (III); this reaction is discribed in greater detail below. It should be noted now, however, that the process of the present invention affords the following very important advantages over the prior art preparation of N-formimidoyl thienamycin: (1) The process invention is very efficient in that it may be conducted in dilute aqueous solutions of thienamycin. Since thienamycin is obtained from aqueous fermentation, this feature of the instant process permits the early derivatization of thienamycin without costly concentration and without the attendant intermolecular degradation which has been documented for thienamycin aqueous solutions. (2) Because of the efficiency of the present invention, large excesses of reagent I are not necessary. (3) An advantage related to items (1) and (2) is that use of reagents I in the permissible range minimizes the development of unwanted by-products of reaction which had plagued prior art processes. Typical of such unwanted by-products is the dimer (IV).

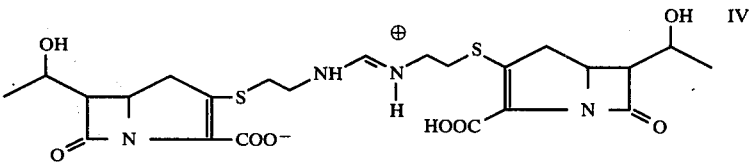

(4) The instantly employed reagents I are more stable than reagents employed in prior art processes for the preparation of N-formimidoyl thienamycin.

Thus, in summary, this invention provides an efficient conversion of thienamycin to Nformimidoyl thianamycin. The novel reagents I are prepared by treating an etherial suspension of formamide and the appropriate substituted benzyl alcohol with benzoyl chloride. The reagents I in reaction with thienamycin in an aqueous solution at pH 7–8.5 give the desired N-formimidoyl thienamycin. These benzylic formimidate reagents are superior to known alkyl formimidates in he described formimidoylation of thienamycin as they show increased stability in aqueous solution and produce a minimal amount of the undesired bis-thienamycin formamidine by-product. While applicants are bound by no theory, it appears that the success of the instantly disclosed formimidoylation reagents is attributed to the increased lipophilicity of the resulting formimidate (I), thus improving aqueous stability. The use of benzyl and substituted benzyl moieties also provides a means of increasing the leaving group ability of the alcohol moiety, thus minimizing the amount of unwanted by-products. It should be further noted that the prior art procedure of derivatizing thienamycin in a concentrated aqueous solution at pH 8.5 using, for example methylformimidate hydrochloride was beset by disadvantages. The reagent was rapidly hydrolyzed in aqueous solution, thus a large excess (for example 30 equivalents) of reagent was required. Workup of the final reaction mixture gave the desired N-formimidoyl thienamycin contaminated with as much as 15% of the undesired dimer (structure IV above). This unwanted by-product formation coupled with instability of the reagent made this process unattractive.

DETAILED DESCRIPTION OF THE INVENTION

The process of the present invention may conveniently be represented by the following reaction:

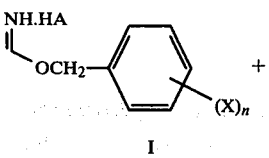 +

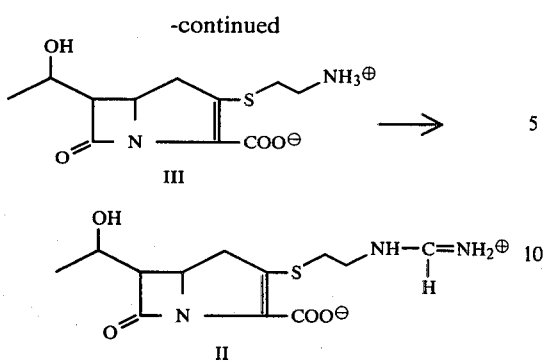

wherein all symbols have previously been defined. Typically, the reaction is run in water at a pH from 7 to 8.5. Typically, the ratio of reagent I. to thienamycin is from 1.5:1 to 10:1, the most preferred reaction ratio being 6 to 1.

The benzylic formimidate reagents have been previously defined. The following describes their convenient synthesis and indicates the most preferred reagents:

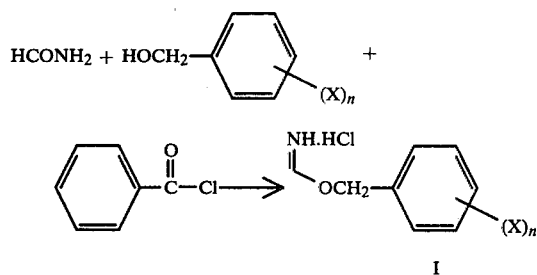

The reagent I is prepared by the reaction of formamide, benzoyl chloride and the desired benzylic alcohol in an etherial solution to give the desired formimidates as stable crystalline salts. In addition to benzoyl chloride the following may be used: alkyl acyl chlorides, aryl acyl chlorides, acyl bromides, or mixed alkyl, aryl acyl chlorides. The following reagents I are especially preferred:

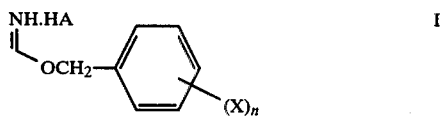

| | A | n | X |
|---|---|---|---|
| (1.) | Cl | 0 | — |
| (2.) | Cl | 1 | ortho-, meta-, or para-nitro |
| (3.) | Cl | 1 | ortho-, meta-, or para-chloro |
| (4.) | Cl | 1 | ortho-, meta-, or para-bromo |
| (5.) | | | ortho-, meta-, or para-loweralkyl |
| (6.) | Cl | 2 | dichloro |
| (7.) | | | dinitro |
| (8.) | | | ortho-, meta-, or para-phenyl |
| (9.) | | | ortho-, meta-, or para-COOR (R = H, loweralkyl) |

EXAMPLE I

I. Preparation of benzyl formimidate hydrochloride

A 3.0 L three-necked flask fitted with an addition funnel, overhead stirrer, and a reflux condenser, is charged with a mixture of benzyl alcohol (125 g, 1.15 mol), formamide (51 g, 1.12 mol), and anhydrous ether (1200 ml). The mixture is stirred vigorously at room temperature (20°-25°) under a nitrogen atmosphere and benzoyl chloride (157 g, 1.12 mol) in 50 ml. of anhydrous ether is added dropwise using the addition funnel. A white precipitate forms after about 50% of the benzoyl chloride had been added. The addition requires approximately 50 minutes.

The reaction mixture is stirred an additional 60 minutes at room temperature. The ether is removed by decantation and 300 ml. of acetic anhydride in 500 ml. of anhydrous ether is added. The mixture is stirred 30 minutes at room temperature. The precipitate is allowed to settle and the ether-acetic anhydride is again removed by decantation. The solid is washed with 500 ml. of ether and dried in vacuo over KOH at 25° for 2 hrs. to give 130 g (67%) of benzyl formimidate hydrochloride as a white solid.

NMR: (DMSO) 5.7 (s,2H,OCH$_2$), 7.5 (s,5H,O), 9.0 (s,1H,HC=N). The product is thermally unstable. It decomposes to formamide and benzyl chloride at 0° and above. However, no appreciable decomposition is detected on storage at −20° for 2 months.

EXAMPLE II

Derivatization of Thienamycin

An aqueous solution of thienamycin (6.0 L, 28 g) is placed in a large beaker and cooled to 0° C. The beaker is equipped with a pH meter and an efficient high speed stirrer. The solution is buffered by adding 1 M, pH 7.0, potassium phosphate buffer. One ml of buffer per 59 ml of concentrate is added to the efficiently stirred solution. The pH is raised to 8.5 by the careful addition of 3 N KOH (KOH is added dropwise via syringe to the stirred solution). The solution is treated with 6 equivalents of solid benzyl formimidate hydrochloride (100 g) in portions while maintaining the pH at 8.5±0.3 by the addition of 3 N KOH (200 ml) using a syringe. The addition required 3-5 min. The reaction mixture is stirred for 6 min. at 0° and then assayed by L.C. to insure completion of the reaction. L.C. assay is accomplished on a 10μ C$_{18}$ Bondapak HPLC column, eluting with 0.01 M, pH 7, potassium phosphate buffer. N-formimidoyl thienamycin and dimer contents are determined by comparison to authentic sample standard. The L.C. assay reveals the presence of 28 g (90%) N-formimidoyl thienamycin and approximately 5% dimer bis-thienamycin formamidine.

What is claimed is:

1. A process for preparing N-formimidoyl thienamycin comprising reacting:

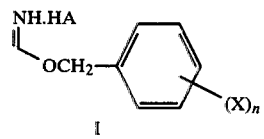

with

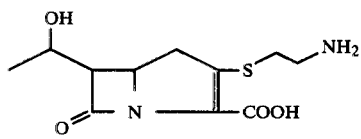

in water at a pH from 7 to 8.5; wherein A is an anion; X is independently selected from the group consisting of nitro, halo (chloro, bromo, fluoro, and iodo), loweralkyl having from one to six carbon atoms, phenyl, and phenylalkyl having from 7–12 carbon atoms, and —COOR, wherein R is hydrogen or loweralkyl having from one to six carbon atoms; and n is 0, 1 or 2.

* * * * *